United States Patent [19]

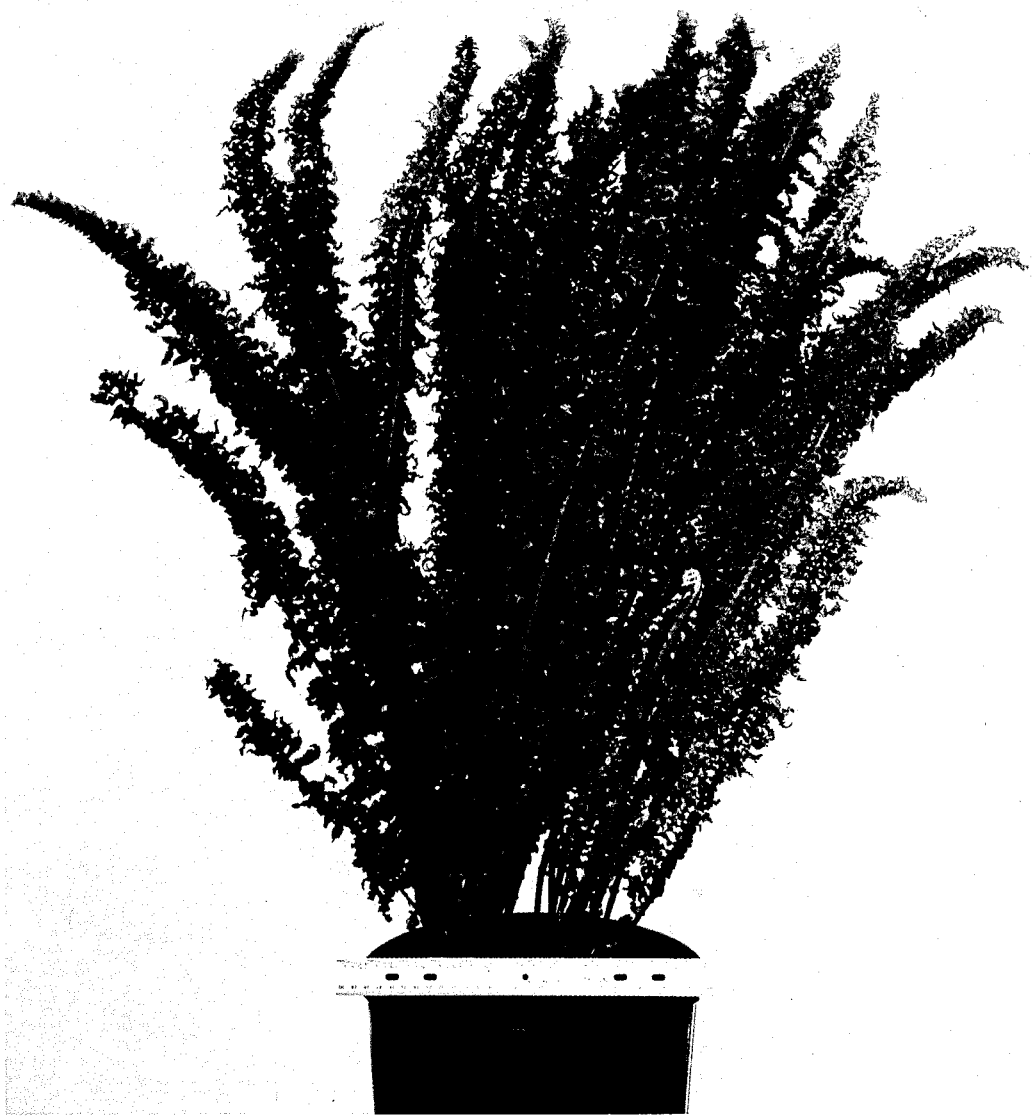

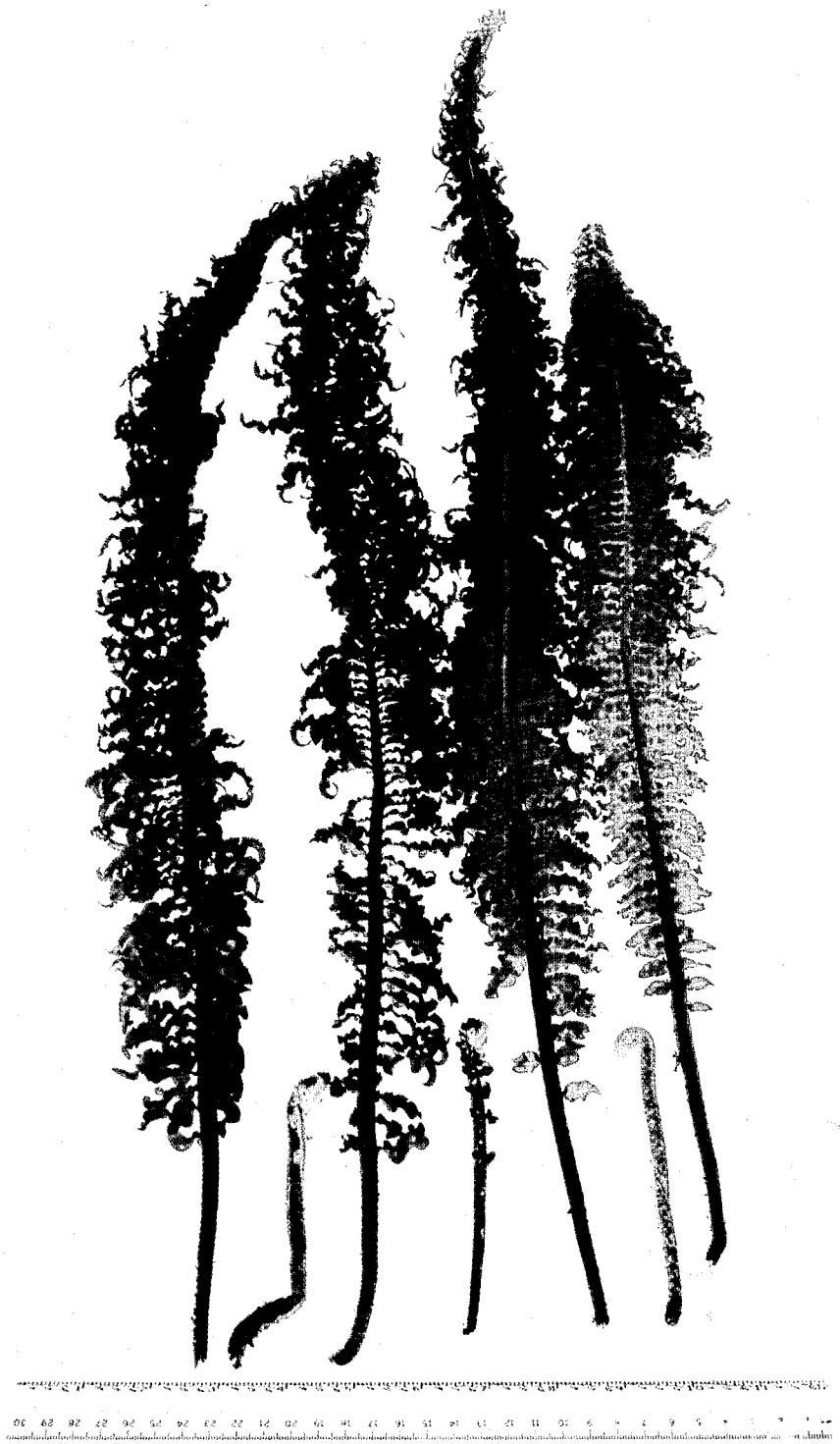

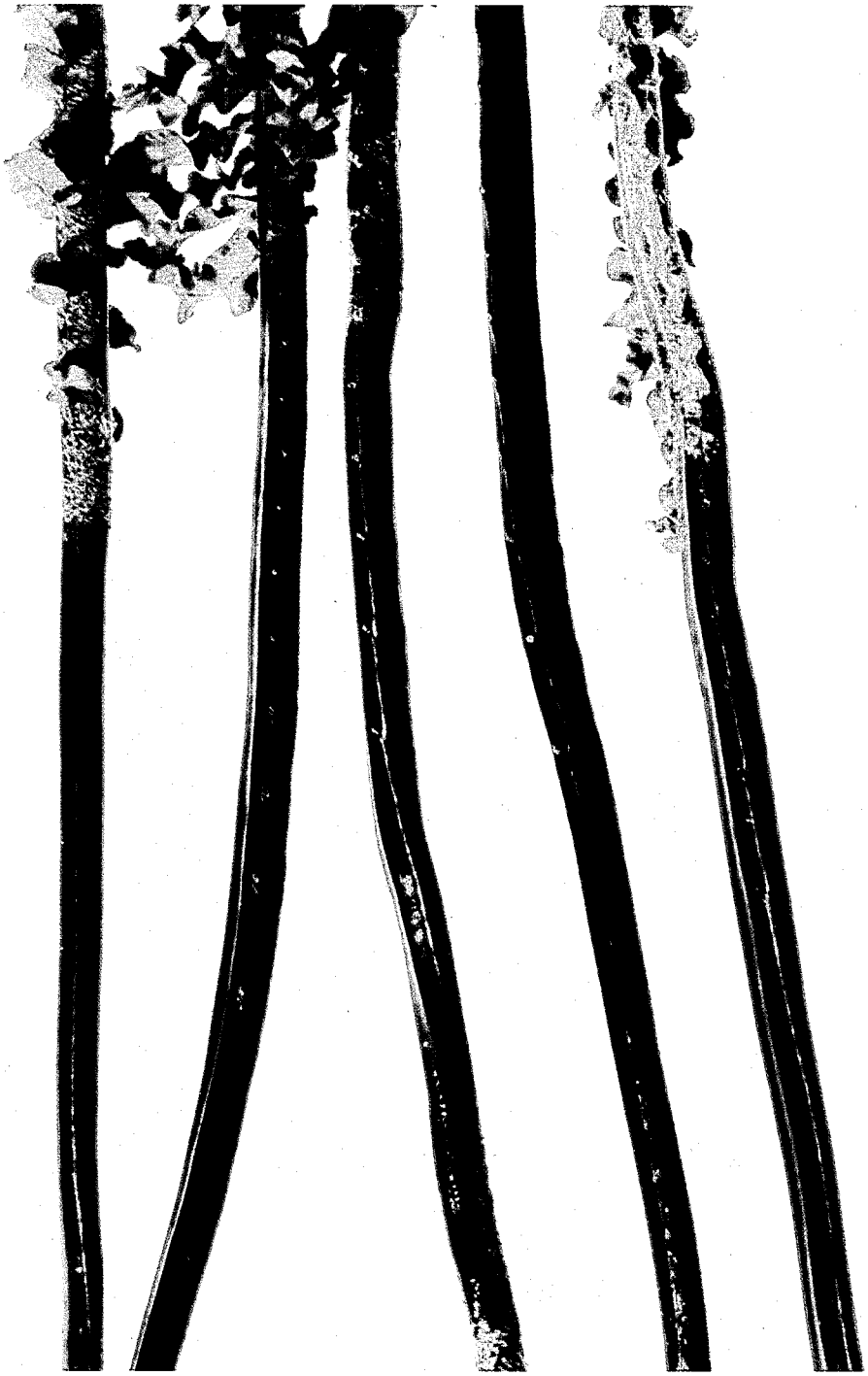

Biggers

[11] Plant 4,010

[45] Jan. 18, 1977

[54] PLANT OF THE FERN FAMILY

[76] Inventor: Donald L. Biggers, Rte. 1, Box 107, Winter Garden, Fla. 32787

[21] Appl. No.: 651,538

[22] Filed: Jan. 22, 1976

[51] Int. Cl.[2] ..... A01H 9/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new plant variety of the fern family has fronds that facilitate their use as fillers and background in long cut flower displays and arrangements and provides specimens during the sporophyte generation with a rosette arrangement of long, erect, robust, pinnately compound mature fronds which have curly, relatively short pinnae that are inserted in a compact arrangement on a long, erect, robust and relatively thick rachis. The rachis and stipe are heavily endowed with hairs and the stipe has a pair of longitudinally extending thin stripes which continue along the pinna insertions on the rachis and which in color are dominated by reddish orange, brown, brownish orange, orange, yellowish brown, orange yellow and/or olive brown hues.

6 Drawing Figures

The invention relates to a new and distinct plant variety of the fern (Polypodiaceae) family and which has been named the *Nephrolepis exaltata* 'Erect' by the inventor.

Plant varieties of the fern family commonly appear in the marketplace and many varieties are of unknown origin but, nevertheless, are endowed with characteristics that provide greater or lesser appeal to the general purchasing public. Some varieties are sold as potted foliage plants while the fronds of yet other varieties are used as background and/or fillers in floral arrangements and cut flower displays.

Most of the fronds used in such arrangements and displays have a delicate appearance and exhibit curvature characteristics that limit their use to medium and short stem cut flower displays and arrangements. Although varieties with long erect fronds are known, their use in long stem cut flower displays and arrangements is usually avoided because they lack the compact pinna arrangements desired for background and filler purposes. Accordingly, one of the objectives of the invention has been to develop a plant variety of the fern family which is productive of specimens with long and erect fronds at maturity that also have a compact pinna arrangement which renders them suitable for use as fillers and background in long stem cut flower displays and arrangements. The objective of the invention has been fully realized as will be evident from the following detailed disclosure.

Specimens of the new and distinct plant variety of the fern family are characterized by a growth habit which provides specimens with a rosette arrangement of long, erect, robust appearing, pinnately compound mature fronds. The fronds have curly, relatively short pinnae that are inserted in a compact arrangement on a long, erect, robust and relatively thick rachis. The stipe and rachis are both heavily endowed with hairs, and the stipe has a pair of longitudinally extending thin stripes which are generally located between the abaxial and adaxial sides of the stipe and which continue distally of the frond insertion along the pinna insertions on the rachis. These thin stripes are in color dominated by reddish orange, brown, brownish orange, orange, yellowish brown, orange yellow and/or olive brown hues during early frond maturity.

The new variety appeared in a bed of ferns of the *Nephrolepis exaltata* 'Silver Balls' variety which was under cultivation in a nursery at Winter Garden, Fla., and since the initial discovery of the new variety, has been asexually reproduced by the inventor at the Winter Garden nursery by the propagation of stem cuttings taken from the original plant specimen. Through successive propagations, it has been ascertained that plants of the new variety may be distinguished from those of related varieties known to the inventor by a growth habit which provides specimens with a rosette arrangement of long, erect, robust appearing, pinnately compound mature fronds which have curly, relatively short pinnae that are inserted in a compact arrangement on a long, erect, robust and relatively thick rachis which is heavily endowed with hairs and basally merges with a stipe that is also heavily endowed with hairs. The stipe of the new variety is also characterized by a pair of longitudinally extending thin (narrow) stripes which continue along the pinna insertions on the rachis and which in color are dominated by the hues previously mentioned.

The variety reproduces true from spores, as well as by asexual reproduction and the accompanying drawings serve, by color photographic means, to illustrate the new variety. One color photograph shows a 12 month old specimen of the new variety which was grown in a plastic container under the nursery conditions contemplated hereinafter. Another color photograph shows abaxial and adaxial sides of cut fronds taken from the specimen, and yet another color photograph shows an enlarged view in the stipe and basal area of the rachis of several fronds, a portion of the pinnae and vestiture being removed to expose the thin stripes.

The following is a detailed description of the new plant variety with colors and hues, unless otherwise clearly indicated by the text, being named in accord with the ISCC-NBS Method of Designating Colors (U.S. Dept. of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md.

PLANT DESCRIPTION

I. Name: *Nephrolepis exaltata* 'Erect'.

II. Parentage: Unknown.

III. Classification:

A. Botanic
1. Family: Polypodiaceae (Fern Family).
2. Genus: Nephrolepis.
3. Species: *exaltata*.

B. Commercial—Foliage plant.

IV. Sporophyte Generation (common reference):

A. Form—Terrestrial, herbaceous, shade loving rosette of erect robust appearing fronds.

B. Stems
1. General: Rhizomatous and stoloniferous with adventitious root system.
2. Rhizomes (common reference):
(a) General—Herbaceous and straight to slightly crooked and non-branching when above ground.
(b) Texture (above ground rhizomes)—Villous over most of rhizome with apex area being sericeous and endowed with overlapping appressed hairs that are usually between 1.5 mm and 4 mm in length, the hairs being membranous, broadly lanceolate, with an acute tip and peltate base, and becoming separated and misshapened with age.
(c) Shape—Generally cylindrical.
(d) Size (above ground rhizomes)
(1) Diameter: Usually between 1.5 mm and 5 mm.
(2) Length: Indeterminate.
(e) Color (vestiture removed)—Strong yellow green (2.5 GY 7/8) and/or brilliant yellow green (2.5 GY 8/8) when above ground.

C. Fronds
1. General: Robust, long, erect, exstipulate, pinnately compound, and foliaceous with circinate vernation and having a stipe that merges with a rachis bearing a compact arrangement of curly, relatively short pinnae.
2. Arrangement: Rosette.
3. Shape: Generally linear with attenuate tips and bases.
4. Size:
(a) Length (including stipe)—Usually between 50 cm and 85 cm at maturity.
(b) Width (maximum)—Usually between 6 cm and 14 cm at maturity.
5. Stipe:
(a) General—Herbaceous and fleshy during initial emergence and becoming brittle and hardening with age.
(b) Texture—Heavily endowed with thin, fringed, appressed, lanceolate hairs, orbicular remains of hair attachments, and thread-like matted remains of hairs at maturity.
(c) Shape—Generally cylindrical and increasing in thickness distally of the insertion in the rhizome, and with an adaxial flattening and/or depression commencing at a point offset from the insertion and extending distally into the rachis.
(d) Size
(1) Length: Usually between 6 cm and 18 cm when measured intermediate the insertion and basally located pinna emergence at full maturity.
(2) Diameter:
a. Basal Area—Usually between 3 mm and 5.5 mm in thickness at full maturity.
b. At First Pinna Emergence—Usually between 4 mm and 7.5 mm in thickness at full maturity.
(e) Color (vestiture removed)
(1) General: Basal area has color dominated by red, reddish brown, and/or brown hues that commonly extend distally on the abaxial side of the stipe. Distal area has color on the adaxial side which is dominated by olive, greenish yellow and/or yellow green hues that commonly transcend a pair of longitudinally extending thin stripes, which in color are dominated by reddish orange, brown, brownish orange, orange, yellowish orange, orange yellow and/or olive brown hues, to merge in the abaxial side with distally extending color found in the basal area.
(2) Basal Area Color: Commonly dark grayish red (near 2.5 R 2/2) (2.5 R 3/2) (near 5 R 2/1) (near 5 R 2/2) (5 R 3/2), blackish red (near 2.5 R 2/2) (near 5 R 2/1) (near 5 R 2/2), reddish black (near 5 R 2/1), very dark red (near 2.5 R 2/2) (near 5 R 2/2), dark grayish reddish brown (7.5 R 2/2) (10 R 2/1) (10 R 2/2) (2.5 YR 2/2), grayish reddish brown (7.5 R 3/2) (10 R 3/2) (2.5 YR 3/2), dark grayish brown (5 YR 2/1) and/or moderate reddish brown (10 R 3/4) (10 R 3/6) (2.5 YR 3/4) (2.5 YR 4/4).
(3) Distal Area Color: Commonly light olive (10 Y 5/4) (10 Y 5/6), dark greenish yellow (10 Y 6/6) (near 10 Y 6/8), deep greenish yellow (near 10 Y 6/8), moderate greenish yellow (near 10 Y 7/8), strong greenish yellow (near 10 Y 7/8) (10 Y 7/10), moderate yellow green (2.5 GY 5/6) (2.5 GY 6/6) (2.5 GY 7/6) and/or strong yellow green (2.5 GY 6/8) (2.5 GY 7/8) on adaxial side.
(4) Lateral Stripe Color: Typically moderate reddish orange (10 R 5/8), strong brown (2.5 YR 4/8) (5 YR 4/6), grayish reddish orange (2.5 YR 5/6), brownish orange (2.5 YR 5/8) (near 5 YR 5/6) (5 YR 5/8), moderate orange (near 5 YR 6/6) (5 YR 6/8), light brown (near 5 YR 5/6) (near 5 YR 6/6) (7.5 YR 5/4) (near 7.5 YR 5/6) (near 7.5 YR 6/6), strong yellowish brown (near 7.5 YR 5/6) (10 YR 5/6), dark orange yellow (near 7.5 YR 6/6) (7.5 YR 6/8) (near 10 YR 6/6) (10 YR 6/8) and/or light olive brown (2.5 Y 5/6).

6. Rachis:
(a) General—Herbaceous and fleshy when maturing and rapidly hardening with age.
(b) Texture—Heavily endowed at maturity with thin matted hairs which are commonly light reddish brown (2.5 YR 5/4) (2.5 YR 6/4), light brown (5 YR 5/4) (5 YR 6/4) (7.5 YR 6/4) (near 5 YR 6/6), moderate orange (near 5 YR 6/6), moderate yellowish pink (5 YR 7/4) and/or light yellowish brown (7.5 YR 7/4) (10 YR 7/4) in color.
(c) Shape—Generally cylindrical to approximately keel shaped with a flattened and/or somewhat depressed adaxial surface.
(d) Size
(1) Length: Usually between 45 cm and 75 cm at maturity when measured between apex and basal pinna emergence.

(2) Thickness: Usually between 3 mm and 6 mm in diameter when measured intermediate the apex and basal pinna emergence.

(e) Color (vestiture removed)

(1) General: The adaxial side color is dominated by olive, olive green and/or yellow green hues and the abaxial side color is dominated by greenish yellow and/or yellow green hues. The pair of stripes on the stipe and the color characteristics continue into the rachis and extend longitudinally in patterns of intersection with the pinna emergences. The adaxial side color commonly transcends the stripes to merge with the abaxial side color and provide generally circumferentially extending arcuate streaks of discoloration on the abaxial side.

(2) Adaxial Side Surface Color: Commonly light olive (10 Y 5/4), moderate olive green (2.5 GY 4/4) (5 GY 4/4) (7.5 GY 4/4), strong yellow green (2.5 GY 6/8) (2.5 GY 7/8) (5 GY 6/8) (5 GY 7/8) and/or moderate yellow green (2.5 GY 5/4) (2.5 GY 5/6) (2.5 GY 6/4) (2.5 GY 6/6) (2.5 GY 7/4) (2.5 GY 7/6) (5 GY 5/4) (5 GY 5/6) (5 GY 6/4) (5 GY 6/6) (5 GY 7/4) (5 GY 7/6) (7.5 GY 5/4) (7.5 GY 5/6) (7.5 GY 6/4) (7.5 GY 7/4).

(3) Abaxial Side Surface Color: Commonly dark greenish yellow (7.5 Y 6/6) (10 Y 6/6) (near 10 Y 6/8), moderate greenish yellow (near 7.5 Y 7/8) (10 Y 7/6) (near 10 Y 7/8), strong greenish yellow (near 7.5 GY 7/8) (near 10 Y 7/8), deep greenish yellow (near 10 Y 6/8), moderate yellow green (2.5 GY 5/6) (2.5 GY 6/6) (2.5 GY 7/6) and/or strong yellow green (2.5 GY 6/8) (2.5 GY 7/8) (5 GY 7/8).

7. Pinnae:

(a) General—Sessile, curly, relatively short and foliaceous.

(b) Arrangement—Predominantly alternate with opposite tendencies for some basal and apical pinnae and generally compactly arranged on rachis with distances between pinnae insertions on the same side of rachis usually being between 2 mm and 12 mm.

(c) Shape—Lanceolate with an auriculate base and being curly and commonly exhibiting varying degrees of torsion between the proximal and distal ends.

(d) Margins—Usually undulate and crenate and/or double crenate and sometimes exhibiting serrate tendencies.

(e) Texture—Usually glabrous to slightly villous along margin, moderately to heavily villous along axis and with sori (when present) located along but offset from the margin on the ventral side of the pinna.

(f) Size (at maturity)

(1) General: Relatively short length dimension in comparison to rachis length at maturity.

(2) Length: Usually between 23 mm and 65 mm in the area located intermediate the proximal and distal ends of rachis and with mature apical pinnae being shorter in length but rarely less than 5 mm.

(3) Width (maximum): Usually less than 16 mm.

(g) Color (1) General: Dorsal side color dominated by olive green, green and/or yellowish green hues and ventral side color dominated by yellow green and/or yellowish green hues.

(2) Dorsal Side: Commonly moderate olive green (5 GY 4/4) (7.5 GY 3/4) (7.5 GY 4/4) (7.5 GY 4/6), grayish yellow green (5 GY 5/2), grayish green (10 GY 5/2), moderate yellow green (5 GY 5/4) (5 GY 5/6) (5 GY 6/6) (7.5 GY 5/4) (7.5 GY 5/6) (7.5 GY 6/6), strong yellow green (5 GY 7/8), moderate yellowish green (10 GY 5/4) and/or dark yellowish green (10 GY 3/4) (10 GY 4/4).

(3) Ventral Side: Commonly moderate yellow green (5 GY 5/4) (5 GY 5/6) (5 GY 6/4) (5 GY 6/6) (7.5 GY 5/4) (7.5 GY 5/6) (7.5 GY 6/4) (7.5 GY 6/6), strong yellow green (5 GY 7/8) (7.5 GY 7/8) and/or moderate yellowish green (10 GY 5/4).

(h) Sori (1) General: Usually present on most or all fronds of a rosette and frequently absent on some pinnae of a sori bearing frond. Located, when present, along but offset from the margins on the ventral side of pinna.

(2) Indusium Shape: Usually approximating reniform.

(3) Indusium Size: Usually between 0.5 mm and 1.5 mm at the widest dimension parallel to the ventral surface.

(4) Sporangia: Spherical and stalked with spheroid diameter usually between 0.05 mm and 0.15 mm.

(5) Spores: Generally oval with a diameter usually between 0.01 mm and 0.05 mm.

(6) Color: Commonly light brown (near 5 YR 5/6) (near 7.5 YR 5/6), brownish orange (near 5 YR 5/6) (5 YR 5/8) and/or strong yellowish brown (near 7.5 YR 5/6) (7.5 YR 5/8) when observed without use of magnification.

V. Gametophyte (prothallium):

A. General—Thin, flat and gamete producing.

B. Texture—Minutely rugose with turgid water filled cells.

C. Shape—Approximately heart to reniform and centrally parted to provide two nearly separated but yet joined and nearly equally sized orbiculate ends as viewed perpendicular to the soil surface.

D. Size (at time of emergence of primary leaf of sporophyte generation)—Maximum width parallel to soil surface is usually between 4 mm and 11 mm.

E. Color—Usually moderate yellow green (2.5 GY 6/6) (5 GY 6/4) (5 GY 6/6) (5 GY 7/6).

The above description is based on observations made during the months of October and November of well fertilized plants of the sporophyte generation that ranged from 6 to 8 months in age (from initial propagation) and which were grown under 85% shaded nursery conditions in the Winter Garden, Florida area and wherein temperatures are maintained from about 65° to 85° F. during the winter months and from about 75° to 95° F. during the summer months.

The following is a general description of a plant specimen of the new variety which was propagated and grown under the above nursery conditions, the description being taken in the month of November.

I. General:

A. Plant Age—10 months.

B. Soil—Natural Florida peat maintained in an above ground growing bed.

II. Stems:

A. General—Unbranched and producing three new rosettes.

B. Number—5 above ground.

C. Size (above ground)

1. Diameter: 1.6 mm to 4.7 mm with average thickness of 3.9 mm.
2. Length: From 6 cm to 18 cm with an average length of 11.8 cm.

D. Color—Strong yellow green (2.5 GY 7/8).

III. Fronds:

A. General

1. Number of mature fronds: 9.
2. Number of immature fronds: 5.

B. Size (mature fronds)

1. Length: From 34.3 cm to 81.3 cm with an average length of 69 cm.
2. Width (maximum): From 7 cm to 9 cm with an average maximum width of 8.3 cm.

C. Stipe

1. Size (mature fronds):
   (a) Diameter (thickness)
      (1) Basal Area: From 2.5 mm to 5 mm with an average of 4.1 mm.
      (2) At First Pinna Emergence: From 4 mm to 6.5 mm with an average of 5.1 mm.
   (b) Length—From 6 cm to 17 cm with an average of 13.3 cm.
2. Color (mature fronds):
   (a) Basal Area—Dark grayish red (near 2.5 R 2/2) (2.5 R 3/2) (near 5 R 2/1) (near 5 R 2/2) (5 R 3/2), blackish red (near 2.5 R 2/2) (near 5 R 2/1) (near 5 R 2/2), reddish black (near 5 R 2/1) and very dark red (near 2.5 R 2/2) (near 5 R 2/2).
   (b) Lateral Stripes—Strong brown (2.5 YR 4/8) (5 YR 4/6), grayish reddish orange (2.5 YR 5/6), brownish orange (near 5 YR 5/6), light brown (near 5 YR 5/6) (near 7.5 YR 6/6), strong yellowish brown (near 7.5 YR 5/6) and dark orange yellow (near 7.5 YR 6/6).
   (c) Distal Area (adaxial side)—Light olive (10 Y 5/4) (10 Y 5/6) and moderate yellow green (2.5 GY 5/6) (2.5 GY 6/6).

D. Rachis (mature fronds)

1. Size:
   (a) Length—from 46.7 cm to 73 cm with an average of 62.4 cm.
   (b) Diameter or Thickness (intermediate apex and first pinna emergence)—From 3.1 mm to 5.8 mm with an average of 4.7 mm.
2. Color:
   (a) Adaxial Surface—Moderate yellow green (2.5 GY 5/4) (2.5 GY 5/6) (2.5 GY 6/4) (2.5 GY 6/6) (5 GY 5/4) (5 GY 5/6) (5 GY 6/4) (5 GY 6/6) (7.5 GY 5/4) (7.5 GY 5/6) (7.5 GY 6/4).
   (b) Abaxial Surface—Moderate greenish yellow (near 7.5 Y 7/8) (10 Y 7/6) (near 10 Y 7/8), moderate yellow green (2.5 GY 7/6) (2.5 GY 6/6) (2.5 GY 5/6), strong yellow green (2.5 GY 7/8) (2.5 GY 6/8) (5 GY 7/8) and strong yellowish green (10 Y 7/8) (near 7.5 Y 7/8).
   (c) Lateral Stripes—Same as on stipes.

E. Pinnae (mature fronds)

1. Number: 182 per frond (average).
2. Length: From 7.5 mm to 62.5 mm with an average of 48 mm.
3. Width: From 4 mm to 14.5 mm with an average of 11 mm.
4. Color:
   (a) Dorsal Surface—Moderate olive green (5 GY 4/4) (7.5 GY 3/4) (7.5 GY 4/4) (7.5 GY 4/6), moderate yellow green (5 GY 5/4) (5 GY 5/6) (7.5 GY 5/4) (7.5 GY 5/6), moderate yellowish green (10 GY 5/4) and dark yellowish green (10 GY 3/4) (10 GY 4/4).
   (b) Ventral Surface—Moderate yellow green (5 GY 5/6) (5 GY 6/4) (7.5 GY 5/4) (7.5 GY 5/6) (7.5 GY 6/4), strong yellow green (7.5 GY 7/8) and moderate yellowish green (10 GY 5/4).

F. Sori

1. Indusium Size: From 0.7 mm to 1.3 mm with an average of 1.0 mm as measured along the widest dimension parallel to pinna surface.
2. Sori per Pinnae Bearing Sori: 46 average.
3. Color: Brownish orange (near 5 YR 5/6) (5 YR 5/8), strong yellowish brown (near 7.5 YR 5/6) (7.5 YR 5/8) and light brown (near 5 YR 5/6) (near 7.5 YR 5/6).

I claim:

1. The new and distinct plant variety of the fern family substantially as herein described and characterized by a growth habit providing specimens during the sporophyte generation with a rosette arrangement of long, erect, robust, pinnately compound, mature fronds which have curly, relatively short pinnae that are inserted in a compact arrangement on a long, erect, robust and relatively thick rachis which is heavily endowed with hairs and basally merges with a stipe that is also heavily endowed with hairs, the stipe having a pair of longitudinally extending thin stripes which continue along the pinna insertions on the rachis and which in color are dominated during early frond maturity by reddish orange, brown, brownish orange, orange, yellowish brown, orange yellow and/or olive brown hues.

* * * * *

UNITED STATES PATENT AND TRADEMARK OFFICE

CERTIFICATE OF CORRECTION

PATENT NO. : Plant 4,010
DATED : January 18, 1977
INVENTOR(S) : Donald L. Biggers It is certified that error appears in the above-identified patent and that said Letters Patent are hereby corrected as shown below:

Column 8, Line 44, after "described", insert -- and illustrated --

Signed and Sealed this

Twenty-first Day of June 1977

[SEAL]

*Attest:*

RUTH C. MASON
*Attesting Officer*

C. MARSHALL DANN
*Commissioner of Patents and Trademarks*